United States Patent
Aubart et al.

(10) Patent No.: US 7,745,637 B2
(45) Date of Patent: Jun. 29, 2010

(54) PEPTIDE DEFORMYLASE INHIBITORS

(75) Inventors: Kelly M. Aubart, Collegeville, PA (US); Ajita Bhat, Andover, MA (US); Sigfried B. Christensen, IV, Collegeville, PA (US); Jack D. Leber, Collegeville, PA (US); Xiangmin Liao, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 11/675,788

(22) Filed: Feb. 16, 2007

(65) Prior Publication Data
US 2007/0155810 A1    Jul. 5, 2007

(51) Int. Cl.
*A61K 31/4166* (2006.01)
*C07D 233/78* (2006.01)

(52) U.S. Cl. .................. 548/319.5; 514/389; 514/391; 514/392

(58) Field of Classification Search ............... 548/319.5
See application file for complete search history.

(56) References Cited

U.S. PATENT DOCUMENTS

| 5,712,300 A | 1/1998 | Jacobsen | 514/389 |
| 6,495,548 B1 | 12/2002 | Duan | 514/231.5 |
| 6,825,215 B2 | 11/2004 | Chen et al. | 514/314 |

FOREIGN PATENT DOCUMENTS

| WO | WO 97/32846 A1 | 9/1997 |
| WO | WO 02/28829 A2 | 4/2002 |

OTHER PUBLICATIONS

Harris et al., Acta Crystallographica, Section D: Biological Crystallography (Dec. 2002), D58 (12), pp. 2153-2156.
Fenesy, The Mount Sinai Journal of Medicine, vol. 65, Nos. 5&6, pp. 362-369, Oct./Nov. 1998.

*Primary Examiner*—Laura L. Stockton
(74) *Attorney, Agent, or Firm*—Laura K. Madden; Theodore R. Furman

(57) ABSTRACT

Novel PDF inhibitors and novel methods for their use are provided.

4 Claims, 1 Drawing Sheet

Figure 1. The methionine cycle.
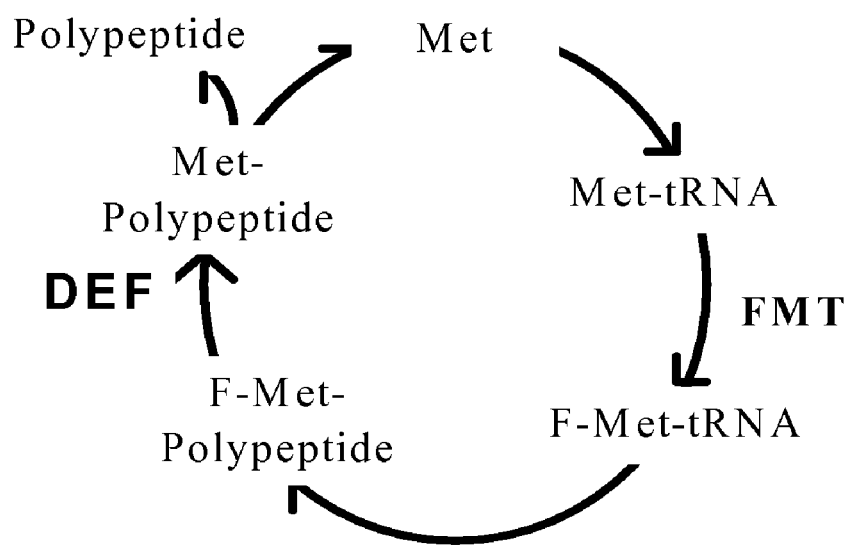

PEPTIDE DEFORMYLASE INHIBITORS

FIELD OF THE INVENTION

The present invention relates to the use of novel antibacterial N-formyl-N-hydroxylamine compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-Met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1)

To date, polypeptide deformylase homologous genes have been found in bacteria, in chloroplast-containing plants, in mice and in humans. The plant proteins are nuclear encoded but appear to carry a chloroplast localization signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel T. 2000, Parasitology Today, 16(4), 165-168).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al, 1997, Journal of Molecular Biology, 267, 749-761).

PDF is recognized to be an attractive anti-bacterial target, as this enzyme has been demonstrated to be essential for bacterial growth in vitro (Mazel, D. et al, EMBO J. 13 (4), 914-923, 1994), is not believed to be involved in eukaryotic protein synthesis (Rajagopalan et al, J. Am. Chem. Soc. 119, 12418-12419, 1997), and is universally conserved in prokaryotes (Kozak, M. Microbiol. Rev. 47, 1-45, 1983). Therefore PDF inhibitors can potentially serve as broad spectrum antibacterial agents.

SUMMARY OF THE INVENTION

The present invention involves novel antibacterial compounds represented by Formula (I) hereinbelow and their use as PDF inhibitors.

BRIEF DESCRIPTION OF THE DRAWINGS

FIG. 1: Provides a graph of the methionine cycle.

DETAILED DESCRIPTION OF THE INVENTION

The compounds useful in the present methods are selected from Formula (I) hereinbelow:

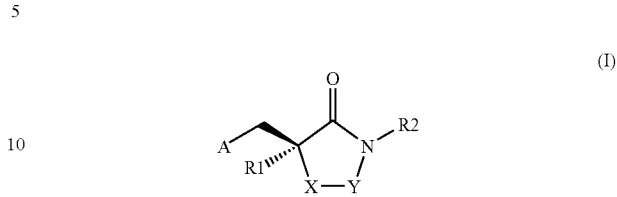

wherein,
R1 is selected from the group consisting of $C_1$-$C_9$alkyl, $C_{1-2}$alkylAr, and Ar;
R2 is selected from the group consisting of hydrogen, $C_1$-$C_9$alkyl, $C_{1-4}$alkylAr', NR4, NC(O)R4, $C_{2-4}$alkylNR3R4, $C_{1-3}$alkylC(O)NR3R4, $C_{1-3}$alkylC(O)Ar', $C_{2-3}$alkylNHC(O)NR3R4, $C_{2-3}$alkylNHC(O)Ar', and $C_{1-2}$alkylSO2R4;
R3 is selected from the group consisting of $C_1$-$C_9$alkyl, $C_{1-2}$alkylAr, and Ar;
R4 is R3, Ar', or R4 may be taken together with R3 and the nitrogen atom to which they are attached to form a heterocyclic ring which is optionally substituted with one, two, or three substituents selected from the group consisting of $C_{1-3}$alkyl, aryl, $C_{1-3}$alkoxy (optionally substituted by one to three F), aryloxy, carboxy, oxo, hydroxy, amino, nitro, and cyano, or which may be optionally fused to an aryl, a heteroaryl, or a second heterocyclic ring;
Ar is selected from the group consisting of phenyl, furyl, and thienyl, all of which can be optionally substituted with one, two, or three substituents selected from the group consisting of: $C_1$-$C_3$alkyl, CN, F, Cl, Br, and I;
Ar' is selected from the group consisting of: phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, pyrrolyl, and pyrimidyl, all of which can be optionally substituted with one, two, or three substituents from the group consisting of: $C_1$-$C_6$alkyl, $C_1$-$C_6$alkoxy, $(CH_2)_{0-5}CO_2R1$, $C(O)N(R1)_2$, CN, $(CH_2)_{0-5}OH$, $NO_2$, F, Cl, Br, I, $CF_3$, $N(R1)_2$, and NHC(O)R1;
A is selected from the group of C(O)NHOH or N(CHO)OH;
X is NH, when Y is C(O), or X is CH2 when Y is C(O) or CH2.

As used herein, "alkyl" refers to an optionally substituted hydrocarbon group joined together by carbon-carbon bonds. The alkyl hydrocarbon group may be linear, branched or cyclic.

As used herein, "aryl" refers to an optionally substituted aromatic group with at least one ring having a conjugated pi-electron system, containing up to two conjugated or fused ring systems. "Aryl" includes carbocyclic aryl, heterocyclic aryl and biaryl groups, all of which may be optionally substituted.

As used herein, "heterocyclic" refers to a three to seven-membered ring containing one or more heteroatomic moieties selected from S, SO, $SO_2$, O, or N. Such a ring can be saturated or have one or more degrees of unsaturation. Examples of "heterocyclic" moieties include, but are not limited to, morpholinyl, piperidinyl, and piperazinyl.

Preferred compounds useful in the present invention are selected from the group consisting of:
N-[(S)-1-Benzyl-4-pentyl-2,5-dioxoimidazolidin-4-ylmethyl]-N-hydroxyformamide;

N-[(S)-1,4-Dibenzyl-2,5-dioxoimidazolidin-4-ylmethyl]-N-hydroxyformamide;

N-[(S)-1-Benzyl-4-butyl-2,5-dioxoimidazolidin-4-ylmethyl]-N-hydroxyformamide;

N-[(S)-2,5-Dioxo-4-pentyl-1-phenylimidazolidin-4-ylmethyl]-N-hydroxyformamide;

N-[(S)-4-Butyl-1-(3,4-dichlorobenzyl)-2,5-dioxoimidazolidin-4-ylmethyl]-N-hydroxyformamide;

N-[(S)-4-Butyl-2,5-dioxo-1-(2-oxo-2-phenylethyl)-imidazolidin-4-ylmethyl]-N-hydroxyformamide;

N-[(S)-1-Biphenyl-4-ylmethyl-4-butyl-2,5-dioxoimidazolidin-4-ylmethyl]-N-hydroxyformamide;

N-[(S)-1-Benzyl-4-cyclohexylmethyl-2,5-dioxoimidazolidin-4-ylmethyl]-N-hydroxyformamide;

N-{(S)-4-Butyl-1-[2-(5-chloro-3-methyl-1-benzo[b]thiophen-2-yl)-2-oxoethyl]-2,5-dioxoimidazolidin-4-ylmethyl}-N-hydroxyformamide;

2-{(S)-4-Butyl-4-[(formylhydroxyamino)methyl]-2,5-dioxoimidazolidin-1-yl}-N-(3,5-dichlorophenyl)acetamide;

2-{(S)-4-Butyl-4-[(formylhydroxyamino)methyl]-2,5-dioxoimidazolidin-1-ylmethyl}benzoic acid methyl ester;

N-[(S)-4-Butyl-1-(2-morpholin-4-yl-ethyl)-2,5-dioxoimidazolidin-4-ylmethyl]-N-hydroxyformamide;

N-[(S)-1-(2-Benzofuran-2-yl-2-oxoethyl)-4-butyl-2,5-dioxoimidazolidin-4-ylmethyl]-N-hydroxyformamide; and 2-{(S)-4-Butyl-4-[(formylhydroxyamino)-methyl]-2,5-dioxoimidazolidin-1-ylmethyl}benzoic acid.

Also included in the present invention are pharmaceutically acceptable salts and complexes, such as hydrochloride, hydrobromide, trifluoroacetate, sodium, potassium, and magnesium salts. The compounds of the present invention may contain one or more asymmetric carbon atoms and may exist in racemic and optically active forms. All of these compounds and diastereomers are contemplated to be within the scope of the present invention.

Compounds of Formula (I) may be prepared according to the following representative schemes, which are illustrative of the methods employed and are not intended to limit the scope of the invention as defined in the appended claims. Compounds of Formula (I) can be prepared by a process analogous to Scheme 1.

Scheme 1

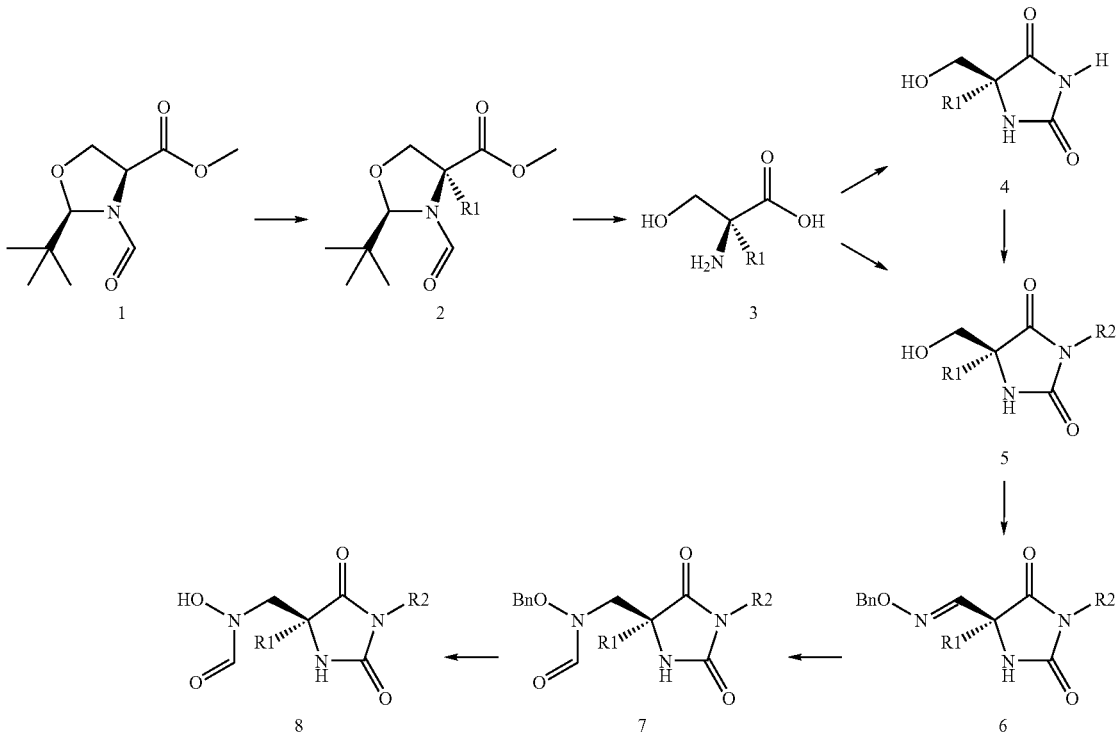

The oxazolidine derivative 1-Scheme-1 can be prepared from L-serine methyl ester as described in the literature [D. Seebach, J. D. Aebi, M. Gander-Coquoz and R. Naef, *Helv. Chim. Acta.*, 70, 1194 (1987)]. Treatment of 1-Scheme-1 with a suitable base such as sodium bis(trimethylsilyl)amide in the presence of a reactive halide R1X in a mixed solvent of tetrahydrofuran/hexamethylphosphoramide (10:1) affords ester 2-Scheme-1, which can be hydrolyzed under acidic conditions to give α-substituted serine 3-Scheme-1. The N-substituted hydantoin derivative 5-Scheme-1 can be prepared by direct treatment of 3-Scheme-1 with an isocyanate R2NCO, or alternatively, treatment of 3-Scheme-1 with potassium cyanate provides hydantoin 4-Scheme-1 which can then be alkylated with a halide R2X. Alcohol 5-Scheme-1 can be oxidized with a suitable reagent such as Dess-Martin periodinane to give the aldehyde which can be treated with O-benzyl hydroxylamine to provide oxime 6-Scheme-1. Reduction of oxime 6-Scheme-1 with sodium cyanoborohydride followed by treatment with the mixed anhydride formed from formic acid and acetic anhydride provides formamide 7-Scheme-1. Finally, N-formyl-N-hydroxylamine 8-Scheme-1 is obtained by hydrogenolysis of 7-Scheme-1 in an alcoholic solvent in the presence of a catalyst such as palladium on activated carbon.

Alternatively, compounds of Formula (I) can be prepared from alcohol 5-Scheme-1 as shown in Scheme 2. Mitsunobu reaction of 5-Scheme-2 affords compound 9-Scheme-2. Removal of the protecting groups under acidic conditions provides hydroxylamine derivative 10-Scheme-2. Treatment of 10-Scheme-2 with the mixed anhydride formed from formic acid and acetic anhydride results in N,O-formylated compound 11-Scheme-2, and removal of the O-formyl group by basic hydrolysis gives N-formyl-N-hydroxylamine 12-Scheme-2.

Scheme 2

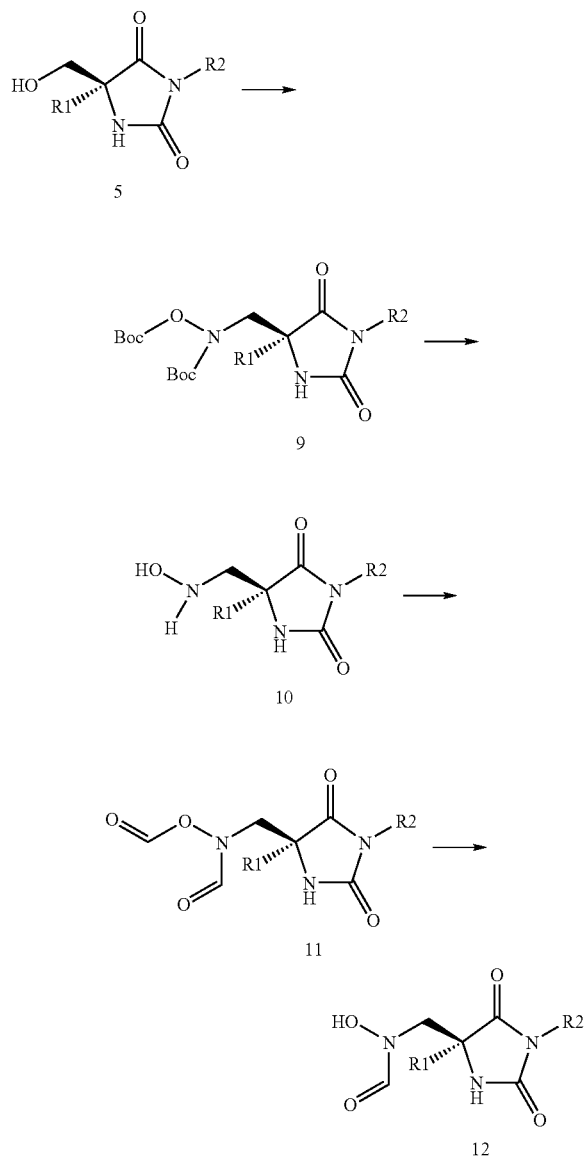

The foregoing may be better understood by reference to the following Examples which illustrate the methods by which the compounds of the invention may be prepared and are not intended to limit the scope of the invention as defined in the appended claims.

EXAMPLE 1

Preparation of N-[(S)-1-benzyl-4-butyl-2,5-dioxoimidazolidin-4-ylmethyl]-N-hydroxyformamide, SB-725291

1a. (2R,4S)-4-Butyl-2-tert-butyl-3-formyloxazolidine-4-carboxylic acid methyl ester To a solution of (2R,4S)-2-tert-butyl-3-formyloxazolidine-4-carboxylic acid methyl ester (4.6 g, 21.4 mmol) [see D. Seebach, J. D. Aebi, M. Gander-Coquoz and R. Naef, *Helv. Chim. Acta.*, 70, 1194 (1987)] in dry THF (120 mL) under $N_2$ was added 1-iodobutane (12.2 mL, 106.8 mmol) and HMPA (12 mL). The mixture was cooled to −78° C. and a solution of sodium bis(trimethylsilyl)amide in THF (1 M, 32 mL, 32 mmol) was added dropwise over 15 minutes. After 2 h, the reaction mixture was warmed to 0° C. and quenched with saturated aqueous $NH_4Cl$ (200 mL). The quenched reaction mixture was diluted with ether (400 mL) and washed with water (3×200 mL) and brine (200 mL), then dried ($Na_2SO_4$) and filtered. Concentration of the filtrate and flash chromatography of the residue (20% ethyl acetate/hexanes) provided the title compound as a pale brown solid (4.0 g, 69%). MS(ES) m/e 272 $[M+H]^+$.

1b. (S)-5-Butyl-5-hydroxymethyl-imidazolidine-2,4-dione

A solution of compound of Example 1a (4.0 g, 14.7 mmol) in 40 mL concentrated aq. HCl/dioxane (1:1) was heated to reflux for 2 h. After cooling to rt, the reaction mixture was concentrated under vacuum and redissolved in water (15 mL). To this solution was added potassium hydroxide (1 g, 17.8 mmol) and potassium cyanate (2.39 g, 29.4 mmol), and the mixture was heated to 115° C. for 1 h. The reaction was cooled to rt, treated slowly with concentrated aq. HCl (5 mL), and then refluxed for 2 h. The solvent was removed under vacuum, and the resulting solid was extracted with $CH_2Cl_2$/$H_2O$ (2:1) (3×20 mL). The combined organic layers were concentrated to give a white solid (4.8 g) which was purified by Gilson automated HPLC to provide the title compound as a white solid (0.85 g, 31%). MS(ES) m/e 187 $[M+H]^+$.

1c. (S)-3-Benzyl-5-butyl-5-hydroxymethyl-imidazolidine-2,4-dione

To a solution of the compound of Example 1b (0.13 g, 0.70 mmol) in DMF (3 mL) was added $K_2CO_3$ (0.1 g, 0.74 mmol) and benzyl bromide (0.087 mL, 0.74 mmol). The reaction mixture was stirred at rt overnight. The solid was filtered off and the organic solution was purified by Gilson automated HPLC to provide the title compound as a white solid (0.14 g, 73%). MS(ES) m/e 277 $[M+H]^+$.

1d. (S)-1-Benzyl-4-butyl-2,5-dioxo-imidazolidine-4-carbaldehyde O-benzyl-oxime

To a stirred solution of the compound of Example 1c (0.14 g, 0.51 mmol) in 10 mL acetonitrile/dichloromethane (1:1) at 0° C. was added Dess-Martin periodinane (0.32 g, 0.77 mmol). The reaction mixture was stirred at 0° C. for 1 h and then warmed to rt. After stirring at rt overnight, the organic solvents were removed under vacuum. The white solid was dissolved in pyridine (10 mL) and treated with O-benzyl hydroxylamine hydrochloride (0.123 g, 0.77 mmol). After 1 h at rt, the reaction mixture was concentrated to dryness. The residue was dissolved in dichloromethane (25 mL) and washed with saturated aq. $NaHCO_3$ (20 mL), water (20 mL), dried ($Na_2SO_4$) and concentrated. The solid was purified by Gilson automated HPLC to provide the title compound as a brownish solid (0.09 g, 47%). MS(ES) m/e 380 [M+H]$^+$.

1e. N-[(S)-1-Benzyl-4-butyl-2,5-dioxo-imidazolidin-4-yl-methyl]-N-benzyloxy-formamide With stirring, sodium cyanoborohydride (45 mg, 0.72 mmol) was added slowly to a solution of the compound of Example 1d (0.09 g, 0.24 mmol) in acetic acid (5 mL). After stirring at rt for 2 h, the reaction mixture was concentrated under vacuum. The residue was taken up in saturated aq. NaHCO$_3$ (15 mL) and extracted with dichloromethane (3×10 mL). The combined organic extractions were dried (Na$_2$SO$_4$), filtered and concentrated to provide the crude (S)-3-Benzyl-5-(benzyloxyamino-methyl)-5-butyl-imidazolidine-2,4-dione, MS(ES) m/e 382 [M+H]$^+$.

The above crude intermediate was dissolved in dichloromethane (5 mL). To this solution was added triethylamine (0.035 mL), followed by freshly prepared mixed anhydride (prepared by heating a mixture of 0.019 mL formic acid and 0.045 mL acetic anhydride at 50° C. for 1 h and cooling to rt). The reaction mixture was stirred at rt for 1 h and then concentrated to dryness. The residue was purified by Gilson automated HPLC to provide the title compound as a white solid (0.06 g, 62%). MS(ES) m/e 410 [M+H]$^+$.

1f. N-[(S)-1-Benzyl-4-butyl-2,5-dioxo-imidazolidin-4-ylmethyl]-N-hydroxyformamide The compound of Example 1e (0.06 g, 0.15 mmol) was dissolved in methanol (5 mL) and stirred under a balloon hydrogen pressure in the presence of palladium on activated carbon (0.02 g) for 4 h. The reaction mixture was filtered and concentrated, and the residue was purified by Gilson automated HPLC to provide the title compound as a white solid (0.04 g, 84%). MS(ES) m/e 320 [M+H]$^+$.

Proceeding in a similar manner, but substituting appropriate intermediates for those described above, the following compounds were made:
N-[(S)-1-Benzyl-4-cyclohexylmethyl-2,5-dioxo-imidazolidin-4-ylmethyl]-N-hydroxyformamide, MS(ES) m/e 360 [M+H]$^+$.
2-{(S)-4-Butyl-4-[(formylhydroxyamino)methyl]-2,5-dioxo-imidazolidin-1-yl}-N-(3,5-dichlorophenyl)acetamide, MS(ES)m/e 431 [M+H]$^+$.
2-{(S)-4-Butyl-4-[(formylhydroxyamino)methyl]-2,5-dioxo-imidazolidin-1-ylmethyl}benzoic acid methyl ester, MS(ES)m/e 378 [M+H]$^+$.
N-[(S)-4-Butyl-1-(2-morpholin-4-yl-ethyl)-2,5-dioxo-imidazolidin-4-ylmethyl]-N-hydroxyformamide, MS(ES) m/e 343 [M+H]$^+$.
2-{(S)-4-Butyl-4-[(formylhydroxyamino)methyl]-2,5-dioxo-imidazolidin-1-ylmethyl}benzoic acid, MS(ES) m/e 364 [M+H]$^+$.

EXAMPLE 2

Preparation of N-[(S)-2,5-Dioxo-4-pentyl-1-phenyl-imidazolidin-4-ylmethyl]-N-hydroxy-formamide, SB-728794

2a. (S)-5-Pentyl-5-hydroxymethyl-3-phenyl-imidazolidine-2,4-dione

Following the procedure of Example 1a, except substituting pentyl iodide for iodobutane, and then following Example 1b, substituting potassium cyanate with phenyl isocyanate, the title compound was prepared as a white solid (75%). MS(ES) m/e 277 [M+H]$^+$.

2b. N-[(S)-2,5-Dioxo-4-pentyl-1-phenyl-imidazolidin-4-ylmethyl]-N-hydroxyformamide Following the procedure of Examples 1d-f, except substituting the compound of Example 1c with the compound of Example 2a, the title compound was prepared as a white solid. MS(ES) m/e 320 [M+H]$^+$.

Proceeding in a similar manner, but substituting appropriate intermediates for those described above, the following compounds were made:
N-[(S)-1-Benzyl-4-pentyl-2,5-dioxo-imidazolidin-4-ylmethyl]-N-hydroxyformamide, MS(ES) m/e 334 [M+H]$^+$.
N-[(S)-1,4-Dibenzyl-2,5-dioxo-imidazolidin-4-ylmethyl]-N-hydroxyformamide, MS(ES) m/e 354 [M+H]$^+$.

EXAMPLE 3

Preparation of N-[(S)-4-Butyl-2,5-dioxo-1-(2-oxo-2-phenyl-ethyl)-imidazolidin-4-ylmethyl]-N-hydroxy-formamide, SB-736063

3a. (S)-5-Butyl-5-hydroxymethyl-3-(2-oxo-2-phenyl-ethyl)-imidazolidine-2,4-dione Following the procedure of Example 1c, except substituting benzyl bromide with 2-bromo-1-phenylethanone, the title compound was prepared as a white solid (93%). MS(ES) m/e 305 [M+H]$^+$.

3b. tert-Butyl-N-[(S)-4-butyl-2,5-dioxo-1-(2-oxo-2-phenyl-ethyl)-imidazolidin-4-ylmethyl]-N-(tert-butoxycarboxycarbonyloxy)carbamate The compound of Example 3a (0.15 g, 0.49 mmol) and tert-butyl N-(tert-butoxycarboxycarbonyloxy)carbamate (0.18 g, 0.74 mmol) were dissolved in THF (3 mL) under N$_2$ at 0° C. To this solution was added a premixed solution of tributyl phosphine (0.19 mL, 0.74 mmol) and di-t-butyl azodicarboxylate (0.176 g, 0.74 mmol) in THF (2 mL) under N$_2$ at 0° C. The reaction mixture was kept at 0° C. for 1 h, warmed up to rt and stirred overnight. The reaction was quenched with saturated aq. NaHCO$_3$ (15 mL) and extracted with dichloromethane (3×10 mL). The combined organic layers were dried (Na$_2$SO$_4$), filtered and concentrated. The residue was purified by Gilson automated HPLC to provide the title compound as a white solid (0.11 g, 42%). MS(ES) m/e 520 [M+H]$^+$.

3c. N-[(S)-4-Butyl-2,5-dioxo-1-(2-oxo-2-phenyl-ethyl)-imidazolidin-4-ylmethyl]-N-hydroxyformamide The compound of Example 3b (0.11 g, 0.21 mmol) was dissolved in 15% TFA/1,2-dichloroethane (5 mL). After stirring at rt for 1 h, the reaction mixture was concentrated under vacuum. The residue was dissolved in dichloromethane (5 mL) and treated with triethylamine (0.3 mL), followed by freshly prepared mixed anhydride (0.031 mL formic acid and 0.069 mL acetic anhydride, 50° C., 1 h). After stirring at rt for 1 h, the organic solvent was removed under vacuum, and methanol (10 mL) was added, followed by saturated aq. Na$_2$CO$_3$ (3 mL) with vigorous stirring. After 3 h, the reaction mixture was concentrated to dryness, and the solid was extracted with 30% methanol/dichloromethane (3×5 mL). The combined extractions were filtered and concentrated, and the resulting residue was purified by Gilson automated HPLC to provide the title compound as a white solid (0.03 g, 41%). MS(ES) m/e 348 [M+H]$^+$.

Proceeding in a similar manner, but substituting appropriate intermediates for those described above, the following compounds were made:

N-[(S)-4-Butyl-1-(3,4-dichlorobenzyl)-2,5-dioxo-imidazolidin-4-ylmethyl]-N-hydroxyformamide, MS(ES) m/e 388 [M+H]$^+$.

N-[(S)-1-Biphenyl-4-ylmethyl-4-butyl-2,5-dioxo-imidazolidin-4-ylmethyl]-N-hydroxyformamide, MS(ES) m/e 396 [M+H]$^+$.

N-{(S)-4-Butyl-1-[2-(5-chloro-3-methyl-1-benzo[b]thiophen-2-yl)-2-oxo-ethyl]-2,5-dioxo-imidazolidin-4-ylmethyl}-N-hydroxyformamide, MS(ES) m/e 452 [M+H]$^+$.

N-[(S)-1-(2-Benzofuran-2-yl-2-oxo-ethyl)-4-butyl-2,5-dioxo-imidazolidin-4-ylmethyl]-N-hydroxyformamide, MS(ES) m/e 388 [M+H]$^+$.

With appropriate manipulation and protection of any chemical functionality, synthesis of the remaining compounds of Formula (I) is accomplished by methods analogous to those described.

The present compounds are useful for the treatment of bacterial infections. In order to use a compound of Formula (I) or a pharmaceutically acceptable salt thereof, it is normally formulated in accordance with standard pharmaceutical practice as a pharmaceutical composition.

Compounds of Formula (I) and their pharmaceutically acceptable salts may be administered in a standard manner for antibiotics, for example orally, parenterally, sub-lingually, dermally, transdermally, rectally, via inhalation or via buccal administration.

Compositions of Formula (I) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg of a compound of Formula (I) or a pharmaceutically acceptable salt thereof calculated as the free acid. Each dosage unit for intranasal administration contains suitably 1-400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg of a compound of Formula (I) or a pharmaceutically acceptable salt thereof calculated as the free acid. The daily dosage regimen for parenteral administration is suitably about 0.001 mg/Kg to 40 mg/Kg of a compound of Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following test:

Biological Assay:

S. aureus or E. coli PDF activity is measured at 25° C., using a continuous enzyme-linked assay developed by Lazennec & Meinnel, (1997) "Formate dehydrogenase-coupled spectrophotometric assay of peptide deformylase" Anal. Biochem. 244, pp. 180-182, with minor modifications. The reaction mixture is contained in 50 uL with 50 mM potassium phosphate buffer (pH7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: Staphylococcus aureus Oxford, Staphylococcus aureus WCUH29, Enterococcus faecalis I, Enterococcus faecalis 7, Haemophilus influenzae Q1, Haemophilus influenzae NEMC1, Moraxella catarrhalis 1502, Streptococcus pneumoniae 1629, Streptococcus pneumoniae N1387, Streptococcus pneumoniae N1387, E. coli 7623 (AcrABEFD+) and E. coli 120 (AcrAB−). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows

What is claimed is:

1. A compound according to Formula (I):

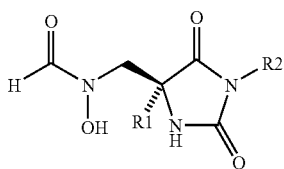

wherein
R1 is selected from the group consisting of $C_1$-$C_9$alkyl, $C_{1-2}$alkylAr, and Ar;
R2 is selected from the group consisting of hydrogen, $C_1$-$C_9$alkyl, $C_{1-4}$alkylAr', NHR4, NHC(O)R4, $C_{2-4}$alkylNR3R4, $C_{1-3}$alkylC(O)NR3R4, $C_{1-3}$alkylC(O)Ar', $C_{2-3}$alkylNHC(O)NR3R4, $C_{2-3}$alkylNHC(O)Ar', and $C_{1-2}$alkylSO$_2$R4;
R3 is selected from the group consisting of C1-$C_9$alkyl, $C_{1-2}$alkylAr, and Ar;
R4 is R3, Ar', or R4 may be taken together with R3 and the nitrogen atom to which they are attached to form a heterocyclic ring which is optionally substituted with one, two, or three substituents each independently selected from the group consisting of $C_{1-3}$alkyl, aryl, $C_{1-3}$alkoxy (optionally substituted by one to three F), aryloxy, carboxy, oxo, hydroxy, amino, nitro, and cyano, or which may be optionally fused to an aryl, a heteroaryl, or a second heterocyclic ring;
Ar is selected from the group consisting of phenyl, furyl, and thienyl, all of which can be optionally substituted with one, two, or three substituents each independently selected from the group consisting of: $C_1$-$C_3$alkyl, CN, F, Cl, Br, and I; and
Ar' is selected from the group consisting of: naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, pyrrolyl, and pyrimidyl, all of which can be optionally substituted with one, two, or three substituents each independently selected from the group consisting of: $C_1$-$C_6$alkyl, $C_1$-$C_6$alkoxy, $(CH_2)_{0-5}CO_2R1$, $C(O)N(R1)_2$, CN, $(CH_2)_{0-5}OH$, $NO_2$, F, Cl, Br, I, $CF_3$, $N(R1)_2$, and NHC(O)R1; or a pharmaceutically acceptable salt thereof.

2. A pharmaceutical composition comprising a compound according to claim 1, or a pharmaceutically acceptable salt thereof, and a pharmaceutically acceptable carrier.

3. A compound selected from the group consisting of:
N-[(S)-2,5-Dioxo-4-pentyl-1-phenyl-imidazolidin-4-yl-methyl]-N-hydroxyformamide;
N-[(S)-1-Biphenyl-4-ylmethyl-4-butyl-2,5-dioxo-imidazolidin-4-ylmethyl]-N-hydroxyformamide;
N-{(S)-4-Butyl-1-[2-(5-chloro-3-methyl-1-benzo[b]thiophen-2-yl)-2-oxo-ethyl]-2,5-dioxo-imidazolidin-4-ylmethyl}-N-hydroxyformamide; and
2-{(S)-4-Butyl-4-[(formyl-hydroxy-amino)methyl]-2,5-dioxo- imidazolidin-1-yl}-N-(3,5-dichlorophenyl)acetamide;
or a pharmaceutically acceptable salt thereof.

4. A pharmaceutical composition comprising a compound according to claim 3, or a pharmaceutically acceptable salt thereof, and a pharmaceutically acceptable carrier.

* * * * *